United States Patent
McGregor et al.

(10) Patent No.: US 10,620,182 B2
(45) Date of Patent: Apr. 14, 2020

(54) TARGET COMPOSITE CORE APPARATUS FOR RADIAL FLOW GEOMETRY

(71) Applicant: Halliburton Energy Services, Inc., Houston, TX (US)

(72) Inventors: Jacob Andrew McGregor, Burleson, TX (US); John Douglas Manning, Alvarado, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 172 days.

(21) Appl. No.: 15/752,528

(22) PCT Filed: Apr. 28, 2017

(86) PCT No.: PCT/US2017/030151
§ 371 (c)(1),
(2) Date: Feb. 13, 2018

(87) PCT Pub. No.: WO2018/199986
PCT Pub. Date: Nov. 1, 2018

(65) Prior Publication Data
US 2019/0011422 A1 Jan. 10, 2019

(51) Int. Cl.
*E21B 43/116* (2006.01)
*G01N 33/24* (2006.01)
(Continued)

(52) U.S. Cl.
CPC .............. *G01N 33/24* (2013.01); *E21B 43/00* (2013.01); *E21B 43/11* (2013.01); *E21B 43/116* (2013.01);
(Continued)

(58) Field of Classification Search
None
See application file for complete search history.

(56) References Cited

U.S. PATENT DOCUMENTS 2,705,418 A * 4/1955 Francis .............. G01N 15/0826
73/38
3,934,455 A * 1/1976 Harrisberger ........ G01N 15/082
436/5
(Continued)

FOREIGN PATENT DOCUMENTS

WO 94/009254 A1 4/1994

OTHER PUBLICATIONS

International Search Report and Written Opinion issued in related PCT Application No. PCT/US2017/030151 dated Jan. 16, 2018, 14 pages.

*Primary Examiner* — Jill E Culler
(74) *Attorney, Agent, or Firm* — Alan Bryson; Baker Botts L.L.P.

(57) ABSTRACT

To optimize the efficiency of a perforating tool system, downhole conditions may be simulated to determine the optimal configuration for the perforating tool system. A simulated wellbore is disposed in a pressure vessel and coupled to a target composite core assembly. A perforating tool system is disposed in the simulated wellbore above the target composite core assembly. The target composite core assembly includes an outer shell. The outer shell comprises a material that supports a rubber bladder or flexible jacket that is disposed about the outer shell. The outer shell isolates the overburden fluid and pressure from the inner core during a radial flow test to more accurately simulate conditions downhole. A parameter of a perforating tool system may be altered based, at least in part, on a result from the radial flow test.

20 Claims, 4 Drawing Sheets

(51) Int. Cl.
*E21B 43/00* (2006.01)
*E21B 43/11* (2006.01)
*E21B 49/00* (2006.01)
*E21B 49/08* (2006.01)
*E21B 49/02* (2006.01)
*G01N 33/28* (2006.01)
*E21B 49/04* (2006.01)

(52) U.S. Cl.
CPC ............ *E21B 49/00* (2013.01); *E21B 49/088* (2013.01); *E21B 49/02* (2013.01); *E21B 49/04* (2013.01); *E21B 49/087* (2013.01); *G01N 33/2823* (2013.01)

(56) References Cited

U.S. PATENT DOCUMENTS

| | | | | |
|---|---|---|---|---|
| 4,799,382 A | * | 1/1989 | Sprunt | G01N 15/088 378/4 |
| 5,226,310 A | * | 7/1993 | Steiger | E21B 49/006 73/38 |
| 5,269,999 A | * | 12/1993 | Smesny | B29C 43/18 264/112 |
| 5,325,921 A | * | 7/1994 | Johnson | C09K 8/08 166/280.1 |
| 5,504,062 A | * | 4/1996 | Johnson | C09K 8/08 507/212 |
| 5,868,030 A | | 2/1999 | Brumley et al. | |
| 5,969,227 A | | 10/1999 | Kenney | |
| 6,401,523 B1 | * | 6/2002 | Fernandes | G01N 33/241 73/38 |
| 9,464,523 B1 | * | 10/2016 | Grove | E21B 49/088 |
| 2005/0150273 A1 | * | 7/2005 | Potter | G01N 3/10 73/38 |
| 2008/0011483 A1 | * | 1/2008 | LaGrange | E21B 43/116 166/299 |
| 2009/0241700 A1 | | 10/2009 | Haggerty et al. | |
| 2012/0325559 A1 | | 12/2012 | Hedges et al. | |

\* cited by examiner

TARGET COMPOSITE CORE APPARATUS FOR RADIAL FLOW GEOMETRY

CROSS-REFERENCE TO RELATED APPLICATION

The present application is a U.S. National Stage Application of International Application No. PCT/US2017/030151 filed Apr. 28, 2017, which is incorporated herein by reference in its entirety for all purposes.

TECHNICAL FIELD

The present disclosure relates generally to evaluation of equipment utilized and operations performed in conjunction with a subterranean well, more particularly, to constructing a target composite core apparatus for flow performance testing of a perforation made in the target composite core.

BACKGROUND

Hydrocarbons, such as oil and gas, are commonly obtained from subterranean formations that may be located onshore or offshore. The development of subterranean operations and the processes involved in removing hydrocarbons from a subterranean formation are complex. Typically, subterranean operations involve a number of different steps such as, for example, drilling a wellbore at a desired well site, treating the wellbore to optimize production of hydrocarbons, and performing the necessary steps to produce and process the hydrocarbons from the subterranean formation. Measurements of the subterranean formation may be made throughout the operations to characterize the formation and aide in making operational decisions. In certain instances, a communication interface of a downhole tool may be used to communicate data associated with measurements of the formation or other downhole parameters.

A perforating tool system is commonly used to maximize the potential recovery of such hydrocarbons. However, for a given operation, the perforating tool system may be selected based on little to no knowledge of the likely downhole charge performance. For example, a selection of a perforating tool system, including the selected explosive or shaped charges, may be based on an American Petroleum Institute Recommended Practices (API RP) 19B Section 1 test data using standard field guns. The tests are conducted in concrete targets shot under surface conditions then the depth of penetration of the perforations is measured. Consequently, the natural conclusion is to assume that the largest penetration and/or exit hole size delivers the best productivity. However, explosive charges may be designed to optimize performance in any material and not just concrete and thus the comparison of performance in concrete to other materials may be misleading.

FIGURES

Some specific exemplary embodiments of the disclosure may be understood by referring, in part, to the following description and the accompanying drawings.

Figure 1:
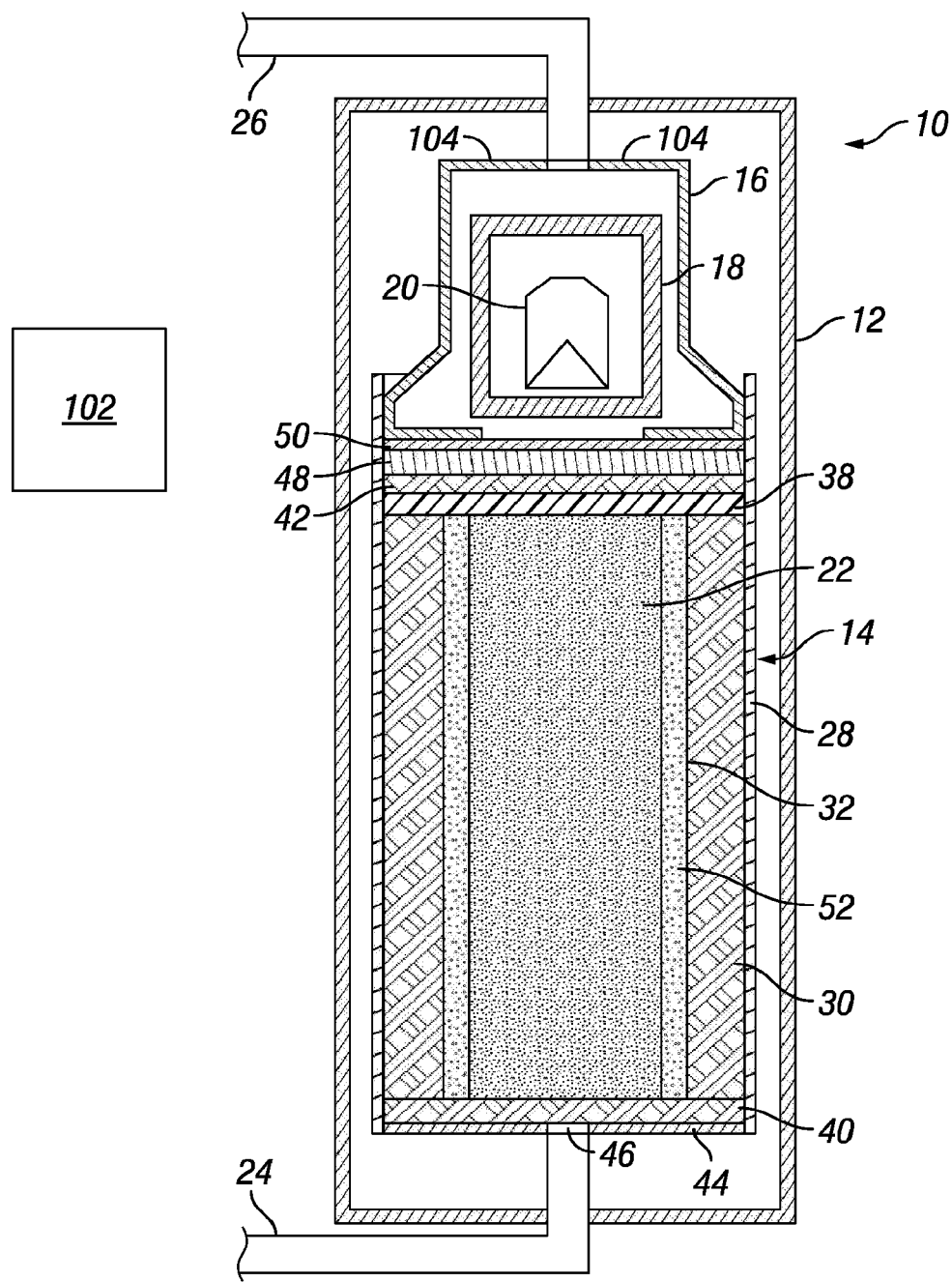
FIG. 1 is a cross-section of a well perforating testing system, according to one or more aspects of the present disclosure.

While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

Explosive or shaped charges may be configured or selected for any type of formation or rock with any one or more properties and for any one or more conditions. Relying on American Petroleum Institute Recommended Practices (API RP) 19B test data may not provide sufficient information for selecting the optimal explosive charges and optimal configuration for the explosive charges. Following API RP 19B Section 2 or Section 4 test procedures, simulation data associated with a perforation of a target composite core at high pressure may be obtained according to one or more aspects of the present disclosure.

A well perforating testing system, for example, an API RP 19B Section 2 and 4 testing system, that simulates one or more downhole conditions according to one or more aspects of the present disclosure provides an improved testing apparatus. A testing apparatus with a small core positioned or disposed inside a larger jacket or rubber bladder with proppant filling the annulus may be prone to bladder failure at the interface of the core and the test fixture the outer core is mounted on. Providing an outer core that is stronger than the proppant packed annulus alone provides support for the rubber bladder at each interface. Having this outer core be weaker than the inner core allows for stress to be passed through the outer core to the proppant packed annulus and to the inner core providing for higher pressure testing of a given sample core and increased volumetric flow rate. One or more flow tests (such as API RP Section 2 and 4 tests) may be performed. The one or more flow tests, for example, one or more radial flow tests may be controlled by an information handling system communicatively coupled to the testing apparatus. Data from the flow tests may be received by the information handling system from one or more sensors of the well perforating testing system and this data may be stored, displayed, graphed, correlated, analyzed or otherwise processed by the information handling system.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components. It may also include one or more interface units capable of transmitting one or more signals to a controller, actuator, or like device.

For the purposes of this disclosure, computer-readable media may include any instrumentality or aggregation of instrumentalities that may retain data and/or instructions for a period of time. Computer-readable media may include, for example, without limitation, storage media such as a direct access storage device (for example, a hard disk drive or floppy disk drive), a sequential access storage device (for example, a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

Illustrative embodiments of the present disclosure are described in detail herein. In the interest of clarity, not all features of an actual implementation may be described in this specification. It will of course be appreciated that in the development of any such actual embodiment, numerous implementation-specific decisions are made to achieve the specific implementation goals, which will vary from one implementation to another. Moreover, it will be appreciated that such a development effort might be complex and time-consuming, but would, nevertheless, be a routine undertaking for those of ordinary skill in the art having the benefit of the present disclosure.

To facilitate a better understanding of the present disclosure, the following examples of certain embodiments are given. In no way should the following examples be read to limit, or define, the scope of the invention. Embodiments of the present disclosure may be applicable to horizontal, vertical, deviated, or otherwise nonlinear wellbores in any type of subterranean formation. Embodiments may be applicable to injection wells as well as production wells, including hydrocarbon wells.

Various aspects of the present disclosure may be implemented in various environments. For example, FIG. 1 is a schematic illustration of a well perforating testing system or testing apparatus, according to one or more aspects of the present disclosure. A well perforating testing system 10, for example, an API RP 19B Section 2 and 4 testing system, includes a pressure vessel 12. Pressure vessel 12 may be pressurized to a desired or predetermined pressure, for example, between approximately 2,000 pounds per square inch (psi) (or about 140.6 kilograms per square centimeter) and approximately 50,000 psi (or about 3,515.3 kilograms per square centimeter) based on one or more conditions of a target wellbore. Any other pressure or range of pressure according to one or more operating conditions or factors may be selected or used. Pressure vessel 12 provides a confining pressure on the target composite core assembly 14.

Well perforating testing system 10 includes a simulated wellbore 16. Target composite core assembly 14 may be coupled to, disposed at our about or positioned adjacent to, proximate to, or below simulated wellbore 16. Simulated wellbore 16 may comprise a perforating tool system 18. In one or more embodiments, the perforating tool system 18 is disposed or secured in an inner portion of the simulated wellbore 16 at or above casing plate 50. Perforating tool system 18 may comprise one or more explosive or shaped charges 20. Simulated wellbore 16 may be pressurized to a desired or predetermined pressure, for example, between approximately 500 psi (or 335.15 kilogram per square centimeter) and 40,000 psi (or about 2,812.3 kilogram per square centimeter). The predetermined pressure may be based, at least in part, on any one or more factors including but not limited to whether perforating will take place in an underbalance condition, an overbalance condition, an extreme overbalance condition, any one or other conditions or any combination thereof.

Explosive charge 20 may be any type of explosive or shaped charged including but not limited to, an explosive charge cyclotrimethylene-trinitramine (RDX), octogen (HMX), Hexanitrostilbene (HNS), 2,6-Bis(Picrylamino)-3, 5-dinitropyridine (very high temperature explosive) (PYX) or similar explosive containing charges.

Well perforating testing system 10 may include a flow system, for example, inlet tubing 24 and outlet tubing 26, for flowing a fluid to apply a pore pressure to the target composite core assembly 14 or inner core 22. The inner core 22 may be a sample field core sample, for example, to simulate an actual formation. The pore pressure may be any desired pressure, for example, between approximately 500 psi and 40,000 psi. While only inlet tubing 24 and outlet tubing 26 of a flow system are illustrated, a flow system may comprise any one or more other components (not shown) including, but not limited to, one or more pumps, one or more filters or filter stages, a heating element, and one or more sensors 104 (for example, flow sensors, pressure sensors, or temperature sensors). The fluid that is pumped through the flow system may be a mineral spirits or any other suitable fluid including, but not limited to, a brine (such as a sodium chloride solution) or a mixture of an oil and brine solution.

Target composite core assembly 14 comprises a flexible jacket 28. Flexible jacket 28 may comprise a rubber bladder, or a rubber or other polymeric or resilient material. Flexible jacket 28 may be substantially cylindrical in shape or any shape suitable for a given testing environment or operation. An outer shell 30 may be positioned or disposed within the flexible jacket 28. Outer shell 30 comprises a core with a center drilled out larger than an inner core 22. The outer shell 30 supports the flexible jacket 28 during a test to isolate the overburden fluid and pressure from the inner core 22. The outer shell 30 comprises a material with a lower unconfined compressive strength than the inner core 22 such that overburden stress in the well perforating testing system 10 is transferred to the inner core 22. For example, the outer shell 30 may comprise a rock material or a rock core. Outer shell 30 may be substantially cylindrical in shape or any other shape suitable to support flexible jacket 28.

Target composite core assembly 14 may comprise an annulus 32 between the outer shell 30 and the inner core 22. Annulus 32 may comprise a proppant 52, for example, a ceramic proppant. The proppant 52 may be packed in the annulus 32. The proppant 52 packed in the annulus 32 may be highly permeable so as not to restrict the flow or surge of a fluid during an operation of the well perforating testing system 10. The proppant 52 packed in the annulus 32 comprises a higher unconfined compressive strength than both the outer shell 30 and the inner core 22.

Target composite core assembly 14 may comprise an inner core 22. The diameter of inner core 22 is based, at least in part, on a desired or predetermined radial testing operation of the wellbore testing assembly 10. The inner core 22 may comprise a material of actual core samples from a reservoir formation of interest (not shown) or may comprise sand having a mineralogical composition that matches or is similar to that of the reservoir formation of interest. For example, the inner core 22 may comprise a sand having similar grain size and density as the reservoir formation of interest and may include additives such as quartz sand or clays (for example, Bentonite). The outer shell 30 allows the well perforating testing system 10 to be pressurized at high pressures without failing the flexible jacket 28. For example, the outer shell 30 is stronger than the proppant 52 that is packed in the annulus 32 which provides support for the flexible jacket 28 but is weaker than the inner core 22, so stress is passed through the outer shell 30, through the proppant 52 that is packed in the annulus 32 to the inner core 22.

Target composite core assembly 14 may comprise a gasket or seal 38 positioned or disposed above the inner core 22, the annulus 32 and the outer shell 30. End plates 40, 42 may be disposed or positioned below and above inner core 22, respectively. In one or more embodiments, an end plate 42 may not be disposed or positioned above inner core 22. End plates 40, 42 may be formed from the same material as outer shell 30 or any other material. End plates 40, 42 may be between approximately one quarter of an inch (at or about 0.635 centimeters) and one inch (at or about 2.54 centimeters) thick or any other suitable thickness. In one or more embodiments, end plate 42 may be positioned or disposed above gasket 38.

A flow distributor plate 44 may be positioned or disposed below end plate 40. Flow distributor plate 44 may be formed from a metal, for example, steel. Flow distributor plate 44 provides an interface between target composite core assembly 14 and the flow system (illustrated as inlet tubing 24 and outlet tubing 26) such that fluid from the flow system may enter target composite core assembly 14 or be fluidically coupled to the target composite core assembly 14 via an opening 46. In one or more embodiments, flow distributor plate 44 may comprise one or more concentric circular grooves and one or more radial connecting grooves. Target composite core assembly 14 may comprise at an upper end a cement coupon 48. Cement coupon 48 may comprise a three quarter inch neat cement or any other cement or material suitable to simulate a wellbore of a reservoir formation of interest. Target composite core assembly 14 may comprise at an upper end a casing plate 50. Casing plate 50 may comprise a one half inch American Society for Testing Materials (ASTM) 4140 steel or any other material or composition suitable to simulate a wellbore of a reservoir formation of interest.

Figure 2:
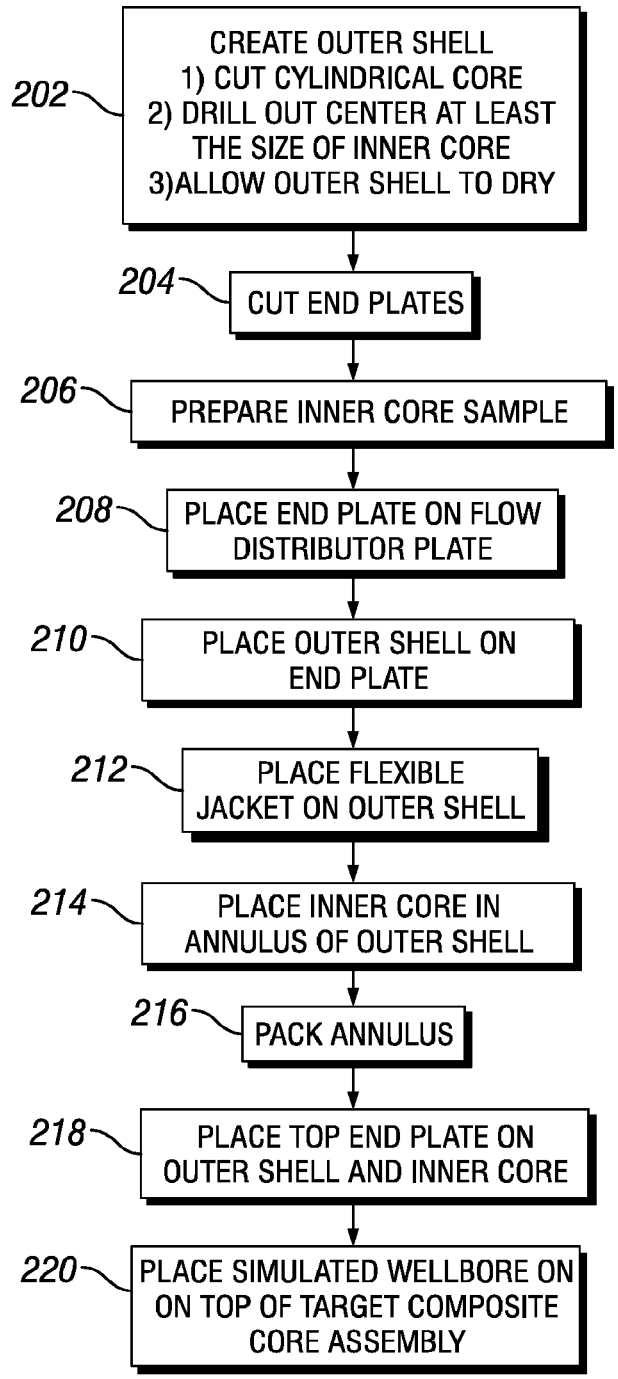
FIG. 2 is a flowchart illustrating an example method for constructing a well perforating testing system for simulation of one or more downhole conditions, according to one or more aspects of the present disclosure.

FIG. 2 is a flowchart illustrating an example method for constructing a well perforating testing system for simulation of one or more downhole conditions, according to one or more aspects of the present disclosure. At step 202 an outer shell (for example, outer shell 30 of FIG. 1) of the well perforating testing system (for example, well perforating testing system 10 of FIG. 1), is created. The outer shell 30 may be created by cutting a cylindrical core from a material. The size of the cylindrical core may be any size according to specific parameters of a given simulation. An inner cylindrical core is then cut from the cylindrical core to create the outer shell 30. The inner cylindrical core is sized to accommodate the selected parameters of the inner core (for example, inner core 22) that is to be disposed within the outer shell 30. The material selected for the outer shell 30 is selected based, at least in part, on the unconfined compressive strength of the material so that the material of the outer shell 30 has a lower unconfined compressive strength than the material that is selected for the inner core 22 of FIG. 1. According to the type of process used to create the outer shell 30, the outer shell 30 may be allowed to dry for a period of time.

Once the outer shell 30 is constructed and dried, assembly of the other components of the well perforating testing system 10 may be completed. At step 204, end plates (for example, end plates 40 and 42 of FIG. 1) for the well perforating testing system 10 are cut. In one or more embodiments, step 204 may occur at, before or during step 202. At step 206, the inner core 22 is prepared for the target composite core assembly, for example, target composite core assembly 14 of FIG. 1. At step 208, end plate 40 is positioned or disposed on the flow distributor plate (for example, flow distributor plate 44 of FIG. 1). At step 210, the outer shell 30 is disposed or positioned on end plate 40. At step 212, the flexible jacket 28 is placed or positioned on the outer shell 30. In one or more embodiments, the flexible jacket 28 and the outer shell 30 are positioned or disposed about an annulus, for example the annulus 32 of FIG. 1.

At step 214, the inner core 22 is centered in the annulus 32 of the outer shell 30. At step 216, the annulus 32 between the outer shell 30 and the inner core 22 is packed with an annulus material, for example, a proppant 52 of FIG. 1, such as a ceramic proppant. The annulus material or proppant 52 may comprise a material with a greater unconfined compressive strength than both the outer shell 30 and the inner core 22. The inner core 22 is disposed within the annulus 32 and the outer shell 30. The inner core 22 comprises a material that has a greater unconfined compressive strength than the outer shell 30. The inner core 22 may be created by cutting a cylindrical core from a predetermined material, for example, a material that is the same or similar to the type of formation of interest or a sandstone that comprises composite material similar to the type of formation of interest. At step 218, a top end plate, for example end plate 42 of FIG. 1, is placed, positioned or disposed on or about the outer shell 30 and the inner core 22. Further, additional material or elements, for example, a gasket or seal, may be positioned or disposed on top of the outer shell 30 and annulus 32, for example, gasket 38 of FIG. 1. In one or more embodiments, the end plate 42 may be positioned or disposed on the gasket 38. At step 220, simulated wellbore 16, for example, simulated wellbore 16 of FIG. 1, is placed, positioned or disposed on top of or about target composite core assembly 14.

Figure 3:
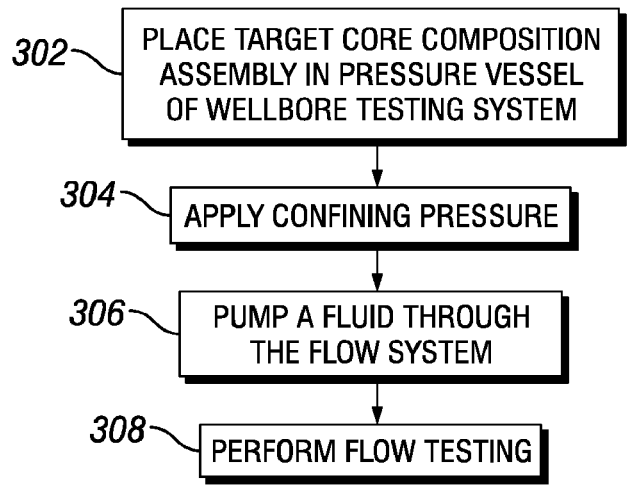
FIG. 3 is a flowchart illustrating an example method for testing and simulation of a perforating tool system, according to one or more aspects of the present disclosure.

FIG. 3 is a flowchart of a method for testing and simulation of a perforating tool system, according to one or more aspects of the present disclosure. In one or more embodiments, a high pressure perforation test, for example, a radial flow test at greater than 15,000 psi confining pressure, (at or about 1,054.6 kilograms per square centimeter) using radial flow boundary conditions on a small diameter field core sample or inner core, may be performed to simulate wellbore conditions for a perforating tool system. At step 302, a target core composition assembly (for example, target composite core assembly 14 of FIG. 1) and simulated wellbore (for example, simulated wellbore 16 of FIG. 1) are associated with a pressure vessel, for example, pressure vessel 12 of FIG. 1. For example, the target composite core assembly 14 and the simulated wellbore 16 may be positioned or disposed within or coupled to the pressure vessel 12 of a well perforating testing system (for example, well perforating testing system 10 of FIG. 1). The target composite core assembly 14 comprises at least an outer shell (for example, outer shell 30 of FIG. 1) that has a lower unconfined compressive strength than an inner core (for example, inner core 22 of FIG. 1) that is disposed within the outer shell 30, an annulus (for example, annulus 32 of FIG. 1) disposed or positioned between the outer shell 30 and the inner core 22, and a flexible jacket (for example flexible jacket 28 of FIG. 1) disposed or positioned about the outer shell 30. For example, the target composite core assembly 14 within the pressure vessel (for example, pressure vessel 12 of FIG. 1) of the well perforating testing system 10 may be as illustrated in FIG. 1.

At step 304, a confining pressure is applied to the inner core 22. The confining pressure is applied by pressurizing a pressure vessel. The confining pressure acts on the exterior of the flexible jacket 28. Flexible jacket 28 transmits a radial confining force to outer shell 30. Outer shell 30 applies at least a portion of the confining force or pressure to the annulus 32 and the inner core 22. A wellbore pressure may also be applied to the well perforating testing system 10 by pressuring the simulated wellbore 16 that comprises the perforating tool system and the explosive charge (for example, perforating tool system 18 and explosive or shaped charge 20, respectively, of FIG. 1) to the predetermined pressure to simulate one or more wellbore conditions. At step 306, a fluid is flowed through the flow system (for example through inlet tubing 24 and outlet tubing 26 of FIG. 1) to apply the pore pressure. At step, 308 one or more flow tests, for example, one or more radial flow tests, are performed or initiated. In one or more embodiments, an information handling system 102 of FIG. 1 may be coupled ((for example, directly or indirectly, mechanically or electrically, or communicatively via a wired or wireless connection) to the well perforating testing system 10 of FIG. 1 to control the one or more flow tests, to receive data from the one or more sensors 104 or both. For example, an explosive or shaped charge (for example, shaped charge 20 of FIG. 1) of a perforating tool system (for example, perforating tool system 18 of FIG. 1) may be detonated to create or form a perforation in inner core 22. In one or more embodiments, the information handling system 102 of FIG. 1 may be coupled (for example, directly or indirectly, mechanically or electrically) to the explosive charge to initiate or activate detonation of the explosive charge.

Once a perforation has been created, the pore pressure may be maintained or adjusted to initiate flow of a fluid through the inner core 22. Once flow is established, any type of flow test may be performed, for example, any API RP Section 2 or 4 tests or any one or more flow tests. In one or more embodiments, detonation of the shaped charge 20 of FIG. 1 and execution or initiation of any one or more flow tests are controlled by an information handling system (for example, information handling system 102 of FIG. 1 or 500 of FIG. 5) that is coupled to or in communication with the well perforating testing system 10. In one or more embodiments, one or more results from the one or more flow tests are communicated to an information handling system 102 of FIG. 1 or 500 of FIG. 5. In one or more embodiments, the one or more results may be displayed on a display, stored in a memory or both of information handling system 500. In one or more embodiments, one or more parameters of a perforating tool system for an environment, such as a well site, are altered or changed based on any of the one or more results from any one or more flow tests. In one or more embodiments, one or more sensors 104 or other measurement devices are coupled to any one or more components of the well perforating testing system 10 and data from the one or more sensors or one or more measurement devices are received by the information handling system 102 of FIG. 1 or 500 of FIG. 5.

The outer shell 30 allows the flow tests, for example, radial flow tests, to be performed at higher pressures compared to typical systems without causing failure to the flexible jacket 28. For example, the outer shell 30 is stronger than the proppant packed annulus 12 alone which supplies support for the flexible jacket 28 where the flexible jacket 28 interfaces to the inner core 22 but the outer shell 30 is weaker than the inner core 22 which results in stress being passed through the outer shell 30 and through the proppant filled annulus 12 to the inner core 22 allowing for higher pressures without a failure to the flexible jacket 28. As the flow tests are able to be performed at higher pressures, the flow tests are more indicative of actual or real world environments.

Figure 4:
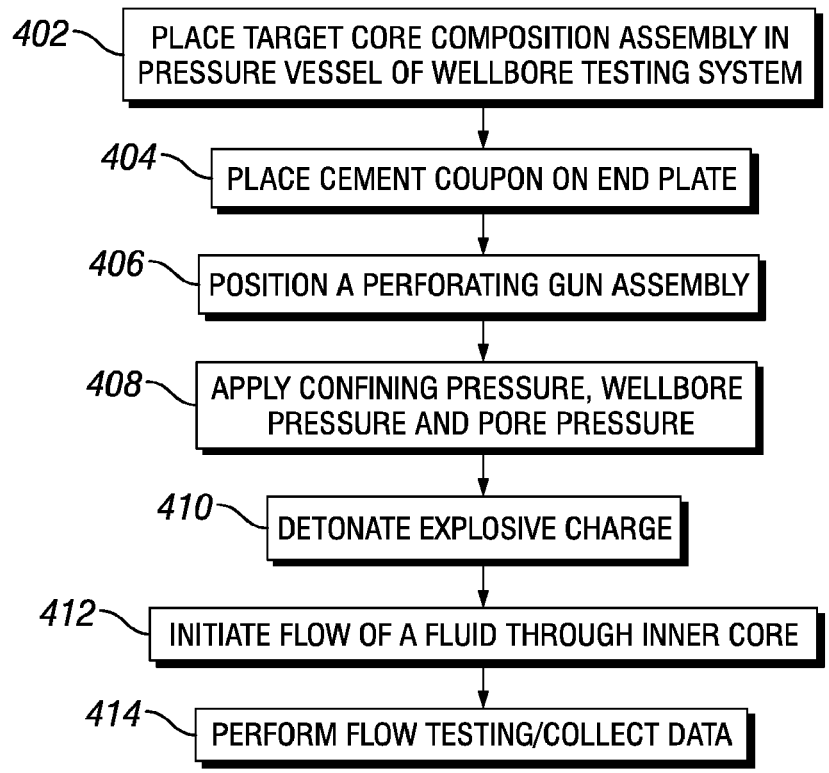
FIG. 4 is a flowchart illustrating an example method for testing and simulation of a perforating tool system, according to one or more aspects of the present disclosure.

FIG. 4 is a flowchart of a method for testing and simulation of a perforating tool system, according to one or more aspects of the present disclosure. At step 402, a target core composition assembly (for example target composite core assembly 14 of FIG. 1) is disposed or positioned within a pressure vessel (for example, pressure vessel 12 of FIG. 1) of well perforating testing system (for example, well perforating testing system 10 of FIG. 1) similar to or the same as discussed above with respect to step 302 of FIG. 3. At step 404, a cement coupon (for example, cement coupon 48 of FIG. 1) is disposed or position on an end plate (for example, end plate 42 of FIG. 1). A casing plate (for example casing plate 50 of FIG. 1) may be disposed or positioned on or about the end plate 42.

At step 406, a perforating gun assembly or a perforating tool system (for example, perforating tool system 18 of FIG. 1) may be disposed or positioned within the well perforating testing system 10. At step 408, a confining pressure, wellbore pressure and pore pressure may be applied similar to or the same as discussed above with respect to steps 304 and 306 of FIG. 3. At step 410, a shaped or explosive charge (for example, shaped charge 20 of FIG. 1) of perforating tool system 18 may be detonated as discussed above with respect to step 308 of FIG. 3. At step 412, flow of a fluid through the inner core 22 is initiated. At step 414, one or more flow tests, for example, one or more radial flow tests, are performed and data is collected similar to or the same as discussed above with respect to step 308 of FIG. 3. In one or more embodiments, one or more parameters of a perforating tool system for an environment, such as a well site, are altered or changed based, at least in part, on one or more results from any one or more flow tests. For example, in one or more embodiments, any one or more of overburden pressure, pore pressure and wellbore pressure may be adjusted, altered or changed. Any one or more parameters may be adjusted to simulate a specific well environment. In one or more embodiments, the casing grade, thickness and hardness may be designed to match the casing used in a specific well or well environment. In one or more embodiments, the cement thickness is adjusted to match the thickness of the specific well or well environment. In one or more embodiments, the perforating tool system for a specific well or well environment may be designed to match the perforating tool system used in the simulation.

Figure 5:
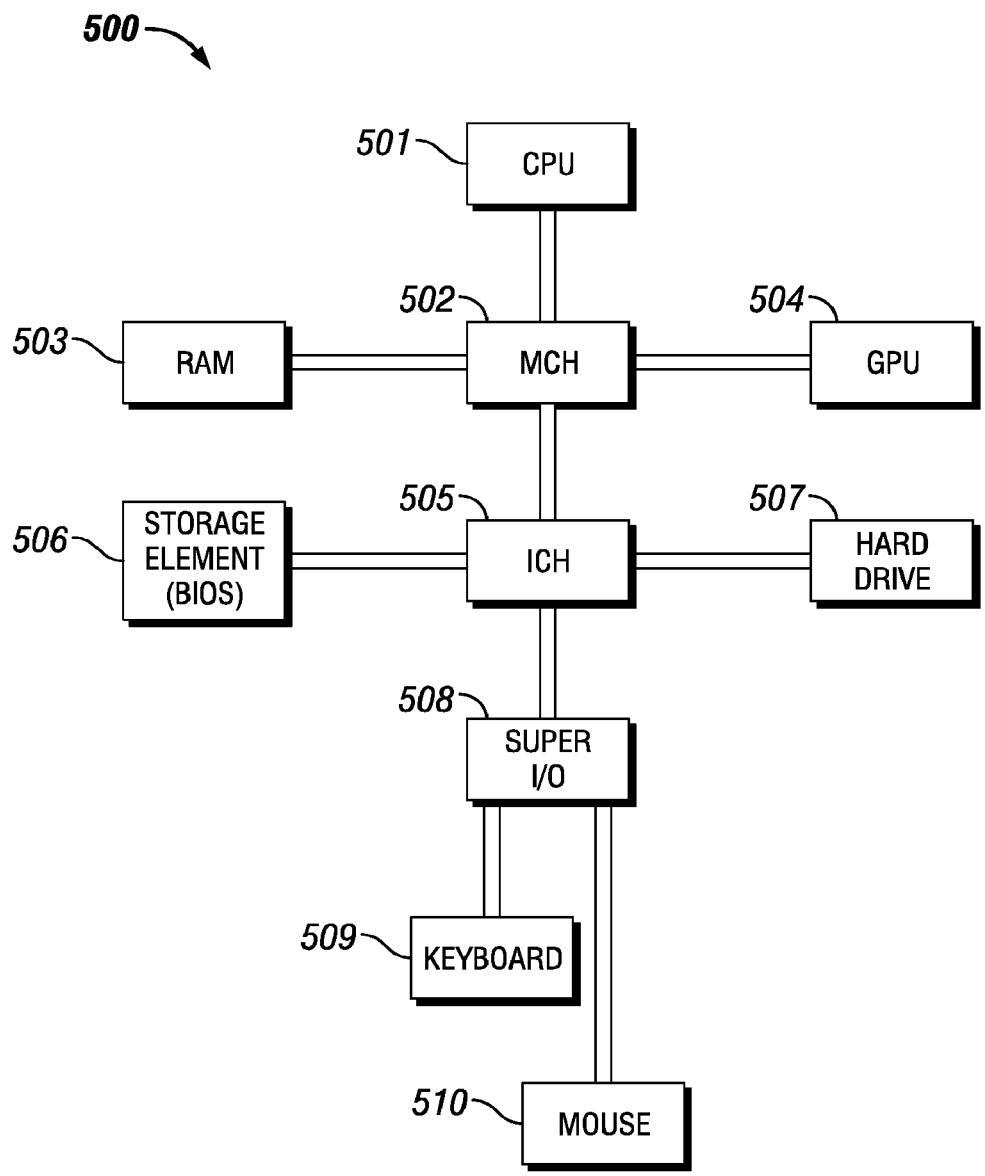
FIG. 5 is a diagram of an information handling system for a well perforating testing system, according to one or more aspects of the present disclosure.

FIG. 5 is a diagram illustrating an example information handling system 500 for a well perforating testing system, according to aspects of the present disclosure. A processor or central processing unit (CPU) 501 of the information handling system 500 is communicatively coupled to a memory controller hub (MCH) or north bridge 502. The processor 501 may include, for example a microprocessor, microcontroller, digital signal processor (DSP), application specific integrated circuit (ASIC), or any other digital or analog circuitry configured to interpret and/or execute program instructions and/or process data. Processor 501 may be configured to interpret and/or execute program instructions or other data retrieved and stored in any memory such as memory 503 or hard drive 507. Program instructions or other data may constitute portions of a software or application for carrying out one or more methods described herein. Memory 503 may include read-only memory (ROM), random access memory (RAM), solid state memory, or disk-based memory. Each memory module may include any system, device or apparatus configured to retain program instructions and/or data for a period of time (for example, computer-readable non-transitory media). For example, instructions from a software or application may be retrieved and stored in memory 503 for execution by processor 501.

Modifications, additions, or omissions may be made to FIG. 5 without departing from the scope of the present disclosure. For example, FIG. 5 shows a particular configuration of components of information handling system 500. However, any suitable configurations of components may be used. For example, components of information handling system 500 may be implemented either as physical or logical components. Furthermore, in some embodiments, functionality associated with components of information handling system 500 may be implemented in special purpose circuits or components. In other embodiments, functionality associated with components of information handling system 500 may be implemented in configurable general purpose circuit or components. For example, components of information handling system 500 may be implemented by configured computer program instructions.

Memory controller hub 502 may include a memory controller for directing information to or from various system memory components within the information handling system 500, such as memory 503, storage element 506, and hard drive 507. The memory controller hub 502 may be coupled to memory 503 and a graphics processing unit 504. Memory controller hub 502 may also be coupled to an I/O controller hub (ICH) or south bridge 505. I/O controller hub 505 is coupled to storage elements of the information handling system 500, including a storage element 506, which may comprise a flash ROM that includes a basic input/output system (BIOS) of the computer system. I/O controller hub 505 is also coupled to the hard drive 507 of the information handling system 500. I/O controller hub 505 may also be coupled to a Super I/O chip 508, which is itself coupled to several of the I/O ports of the computer system, including keyboard 509 and mouse 410.

By performing testing and simulation of a target composite core assembly 14 that simulates a reservoir formation of interest in the controlled environment of well perforating testing system 10, the performance of a perforating tool system 18 may be determined above ground and optimized prior to deployment downhole which reduces costs of a given operation.

In one or more embodiments, a well perforating testing system comprises a pressure vessel, a simulated wellbore associated with the pressure vessel, an outer shell disposed within the pressure vessel, a flexible jacket disposed about the outer shell, an inner core disposed within the outer shell, wherein the inner core comprises a material with an unconfined compressive strength greater than that of the outer shell and an annulus disposed between the inner core and the flexible jacket. In one or more embodiments, the well perforating testing system further comprises a perforating tool system disposed within the well perforating testing system and a shaped charge disposed within the perforating tool system, wherein the shaped charge comprises an explosive that when detonated creates a perforation in the inner core. In one or more embodiments, the annulus comprises a ceramic proppant. In one or more embodiments, the well perforating testing system further comprises a gasket disposed above the inner core. In one or more embodiments, the well perforating testing system further comprises a first end plate disposed below the inner core and a second end plate disposed above the gasket. In one or more embodiments, the well perforating testing system further comprises a flow system coupled to the well perforating testing system, wherein the flow system flows a fluid to apply pore pressure to the inner core, and wherein the flow system comprises an inlet tubing coupled to an opening of a flow distributor plate disposed below the inner core and an outlet tubing coupled to the simulated wellbore. In one or more embodiments, the flexible jacket comprises a rubber bladder.

In one or more embodiments, a method for simulated wellbore testing comprises applying a confining pressure to an inner core of a target composite core assembly by pressurizing a pressure vessel, wherein the target composite core assembly is disposed within the pressure vessel of a well perforating testing system, transmitting a radial confining force by a flexible jacket to an outer shell, wherein the flexible jacket is disposed about the outer shell, and wherein the flexible jacket and the outer shell are disposed about the inner core, and wherein the inner core comprises a material with an unconfined compressive strength greater than that of the outer shell, applying at least a portion of the confining pressure to an annulus disposed about the inner core, creating a perforation in the inner core, performing one or more radial flow tests and altering one or more parameters of a perforating tool system based, at least in part, on one or more results from the one or more radial flow tests. In one or more embodiments, the creating the perforating in the inner core comprises detonating an explosive charge of a perforating tool system. In one or more embodiments, further comprises applying a wellbore pressure to a simulated wellbore disposed adjacent to the target composite core assembly. In one or more embodiments, the method for simulated wellbore testing further comprises adjusting a pore pressure to initiate flow of the fluid through the inner core. In one or more embodiments, the one or more radial flow tests comprise at least one of an American Petroleum Institute Recommended Practices (API RP) 19B section 2 test or an API RP 19B section 4 test. In one or more embodiments, the method for simulated wellbore testing further comprises displaying the one or more results from the one or more radial flow tests.

In one or more embodiments, a system for simulated wellbore testing comprises a pressure vessel, a simulated wellbore disposed within the pressure vessel, an outer shell disposed within the pressure vessel, a flexible jacket disposed about the outer shell, an inner core disposed within the outer shell, wherein the inner core comprises a material with an unconfined compressive strength greater than that of the outer shell, an annulus disposed between the inner core and the flexible jacket and an information handling system communicatively coupled to the simulated wellbore, wherein the information handling system comprising a memory for storing one or more instructions and a processor, wherein the one or more instructions when executed by the processor cause the processor to initiate a radial flow test, receive one or more results from the radial flow test and perform at least one of store the one or more results or display the one or more results. In one or more embodiments, the system for simulated wellbore testing further comprises a perforating tool system disposed within the system and a shaped charge disposed within the perforating tool system, wherein the shaped charge comprises an explosive that when detonated creates a perforation in the inner core. In one or more embodiments, the annulus comprises a ceramic proppant. In one or more embodiments, the system for simulated wellbore testing further comprises a gasket disposed above the inner core. In one or more embodiments, the system for simulated wellbore testing further comprises a first end plate disposed below the inner core and a second end plate disposed above the gasket. In one or more embodiments, the system for simulated wellbore testing further comprises a flow system coupled to the system, wherein the flow system flows a fluid to apply pore pressure to the inner core, and wherein the flow system comprises an inlet tubing coupled to an opening of a flow distributor plate disposed below the inner core and an outlet tubing coupled to the simulated wellbore. In one or more embodiments, the flexible jacket comprises a rubber bladder.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Also, the terms in the claims have their plain, ordinary meaning unless otherwise explicitly and clearly defined by the patentee.

What is claimed is:

1. A well perforating testing system, comprising:
   a pressure vessel;
   a simulated wellbore associated with the pressure vessel;
   an outer shell disposed within the pressure vessel;
   a flexible jacket disposed about the outer shell;
   an inner core disposed within the outer shell, wherein the inner core comprises a material with an unconfined compressive strength greater than that of the outer shell; and
   an annulus disposed between the inner core and the flexible jacket.

2. The well perforating testing system of claim 1, further comprising:
   a perforating tool system disposed within the well perforating testing system; and
   a shaped charge disposed within the perforating tool system, wherein the shaped charge comprises an explosive that when detonated creates a perforation in the inner core.

3. The well perforating testing system of claim 1, wherein the annulus comprises a ceramic proppant.

4. The well perforating testing system of claim 1, further comprising a gasket disposed above the inner core.

5. The well perforating testing system of claim 4, further comprising:
   a first end plate disposed below the inner core; and
   a second end plate disposed above the gasket.

6. The well perforating testing system of claim 1, further comprising:
   a flow system coupled to the well perforating testing system, wherein the flow system flows a fluid to apply pore pressure to the inner core, and wherein the flow system comprises:
      an inlet tubing coupled to an opening of a flow distributor plate disposed below the inner core; and
      an outlet tubing coupled to the simulated wellbore.

7. The well perforating testing system of claim 1, wherein the flexible jacket comprises a rubber bladder.

8. A method for simulated wellbore testing, comprising:
   applying a confining pressure to an inner core of a target composite core assembly by pressurizing a pressure vessel, wherein the target composite core assembly is disposed within the pressure vessel of a well perforating testing system;
   transmitting a radial confining force by a flexible jacket to an outer shell, wherein the flexible jacket is disposed about the outer shell, and wherein the flexible jacket and the outer shell are disposed about the inner core, and wherein the inner core comprises a material with an unconfined compressive strength greater than that of the outer shell;
   applying at least a portion of the confining pressure to an annulus disposed about the inner core;
   applying a pore pressure by flowing a fluid through a flow system of the well perforating testing system;
   creating a perforation in the inner core;
   performing one or more radial flow tests; and
   altering one or more parameters of a perforating tool system based, at least in part, on one or more results from the one or more radial flow tests.

9. The method for simulated wellbore testing of claim 8, wherein the creating the perforation in the inner core comprises detonating an explosive charge of the perforating tool system.

10. The method for simulated wellbore testing of claim 8, further comprising applying a wellbore pressure to a simulated wellbore disposed adjacent to the target composite core assembly.

11. The method for simulated wellbore testing of claim 8, further comprising adjusting a pore pressure to initiate flow of the fluid through the inner core.

12. The method for simulated wellbore testing of claim 8, wherein the one or more radial flow tests comprise at least one of an American Petroleum Institute Recommended Practices (API RP) 19B section 2 test or an API RP 19B section 4 test.

13. The method for simulated wellbore testing of claim 8, further comprising displaying the one or more results from the one or more radial flow tests.

14. A system for simulated wellbore testing, comprising:
    a pressure vessel;
    a simulated wellbore disposed within the pressure vessel;
    an outer shell disposed within the pressure vessel;
    a flexible jacket disposed about the outer shell;
    an inner core disposed within the outer shell, wherein the inner core comprises a material with an unconfined compressive strength greater than that of the outer shell;
    an annulus disposed between the inner core and the flexible jacket; and an information handling system communicatively coupled to the simulated wellbore, wherein the information handling system comprising a memory for storing one or more instructions and a processor, wherein the one or more instructions when executed by the processor cause the processor to:
initiate a radial flow test;
receive one or more results from the radial flow test; and
perform at least one of store the one or more results or display the one or more results.

15. The system for simulated wellbore testing of claim 14, further comprising:
a perforating tool system disposed within the system; and
a shaped charge disposed within the perforating tool system, wherein the shaped charge comprises an explosive that when detonated creates a perforation in the inner core.

16. The system for simulated wellbore testing of claim 14, wherein the annulus comprises a ceramic proppant.

17. The system for simulated wellbore testing of claim 14, further comprising a gasket disposed above the inner core.

18. The system for simulated wellbore testing of claim 17, further comprising:
a first end plate disposed below the inner core; and
a second end plate disposed above the gasket.

19. The system for simulated wellbore testing of claim 14, further comprising:
a flow system coupled to the system, wherein the flow system flows a fluid to apply pore pressure to the inner core, and wherein the flow system comprises:
an inlet tubing coupled to an opening of a flow distributor plate disposed below the inner core; and
an outlet tubing coupled to the simulated wellbore.

20. The system for simulated wellbore testing of claim 14, wherein the flexible jacket comprises a rubber bladder.

\* \* \* \* \*